United States Patent
Carredano et al.

(10) Patent No.: US 10,466,215 B2
(45) Date of Patent: Nov. 5, 2019

(54) METHOD FOR PREDICTING THE SOLUBILITY OF A BUFFER

(71) Applicant: GE Healthcare Bio-Sciences AB, Uppsala (SE)

(72) Inventors: Enrique Carredano, Uppsala (SE); Elenor Strandberg, Sigtuna (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 208 days.

(21) Appl. No.: 15/508,426

(22) PCT Filed: Sep. 22, 2015

(86) PCT No.: PCT/EP2015/071762
§ 371 (c)(1),
(2) Date: Mar. 2, 2017

(87) PCT Pub. No.: WO2016/050566
PCT Pub. Date: Apr. 7, 2016

(65) Prior Publication Data
US 2017/0292937 A1 Oct. 12, 2017

(30) Foreign Application Priority Data
Sep. 29, 2014 (SE) ..................... 1451148

(51) Int. Cl.
*G01N 30/86* (2006.01)
*B01F 15/00* (2006.01)
(Continued)

(52) U.S. Cl.
CPC ......... *G01N 30/8658* (2013.01); *B01D 15/12* (2013.01); *B01F 1/0005* (2013.01);
(Continued)

(58) Field of Classification Search
CPC ............. G01N 2030/347; B01F 1/0038; B01F 1/0005; B01F 15/0022; B01F 15/12; B01F 15/0408; B01F 2001/0044
See application file for complete search history.

(56) References Cited

U.S. PATENT DOCUMENTS

| 5,284,645 A | 2/1994 | Long |
| 2007/0025179 A1 | 2/2007 | Hildreth |
| 2011/0039712 A1* | 2/2011 | Bjorkesten ............. B01D 15/12 506/7 |

FOREIGN PATENT DOCUMENTS

| FR | 2647349 A1 | 11/1990 |
| WO | 02/50531 A2 | 6/2002 |

(Continued)

OTHER PUBLICATIONS

AppliChem Product Sheet. "Biological Buffers" 2008. (Year: 2008).*
(Continued)

*Primary Examiner* — Christopher Adam Hixson
(74) *Attorney, Agent, or Firm* — Eversheds Sutherland (US) LLP (57) ABSTRACT

The invention discloses a method for predicting the solubility of at least one species at a specified pH value in an aqueous buffer comprising at least one weak acid species and/or at least one weak base species. The method comprises the steps of:
a) selecting a start composition of the buffer, giving a start value for the total solute concentration;
b) calculating the concentrations of all ionic species present in the buffer at the specified pH value from the total composition of the buffer and available dissociation constants;
c) calculating the solubility limits of each combination of ionic species present in the buffer from available solubility products, taking the concentrations calculated in step a) into account;
d) comparing the concentrations of all ionic species calculated in step a) with the solubility limits calculated in step b) and determining if any solubility limit is exceeded;
e) if no solubility limit is exceeded, increasing the total solute concentration of the buffer or, if at least one solubility limit is exceeded, decreasing the total solute concentration of the buffer, and;
f) repeating steps b)-e) until a predetermined convergence criteria is met.

14 Claims, 6 Drawing Sheets

(51) Int. Cl.
  *B01F 1/00* (2006.01)
  *G01N 30/34* (2006.01)
  *B01D 15/12* (2006.01)
  *G01N 35/00* (2006.01)
  *B01F 15/04* (2006.01)

(52) U.S. Cl.
  CPC .......... *B01F 1/0011* (2013.01); *B01F 1/0038* (2013.01); *B01F 15/0022* (2013.01); *B01F 15/0408* (2013.01); *G01N 30/34* (2013.01); *G01N 2030/347* (2013.01); *G01N 2035/00465* (2013.01)

(56) References Cited

FOREIGN PATENT DOCUMENTS

WO  2008/028001 A2   3/2008
WO  2009/131524 A1   10/2009

OTHER PUBLICATIONS

Morel, Francois et al. "A numerical method for computing equilibria in aqueous chemical systems." Environmental Science and Technology (1972) 6 58-67 (Year: 1972).*

Debye et al, "Zur Theorie der Elektrolyte", Physikalische Zeitschrift, May 1, 1923, pp. 185-206.

Streng et al, "General Treatment of pH Solubility Profiles of Weak Acids and Bases. II. Evaluation of thermodynamic parameters from the temperature dependence of solubility profiles applied to a zwitterionic compound", International Journal of Pharmaceutics, Elsevier BV NL, vol. 25, No. 2, Jul. 1, 1985.

Streng et al, "Precision tests of a pH-solubility profile computer program", International Journal of Pharmaceutics, vol. 164, No. 1-2, Apr. 1, 1998.

International Search Report and Written Opinion regarding International Application No. PCT/EP2015/071762, dated Jan. 4, 2016, 11 pages.

International-Type Search Report regarding SE Application No. 1451148-9, dated Apr. 16, 2015, 6 pages.

Ledebo, "Acid-Base Correction and Convective Dialysis Therapies," Nephrology Dialysis Transplantation, 2000, 15 (Suppl. 2):45-48.

* cited by examiner

METHOD FOR PREDICTING THE SOLUBILITY OF A BUFFER

CROSS-REFERENCE TO RELATED APPLICATIONS

This application is a filing under 35 U.S.C. 371 of international application number PCT/EP2015/071762, filed Sep. 22, 2015, which claims priority to SE application number 1451148-9, filed Sep. 29, 2014, the entire disclosures of each of which are hereby incorporated by reference.

TECHNICAL FIELD OF THE INVENTION

The present invention relates to preparation of buffers and in particular to a method of predicting solubility limits for buffers. The invention also relates to computer programs and mixing systems useful for preparation of buffers of high concentrations.

BACKGROUND OF THE INVENTION

A buffer solution is typically an aqueous solution containing a mixture of a weak acid and its conjugate base, or a weak base and its conjugate acid, and has the property that the pH of the solution changes very little when a small amount of strong acid or base is added to it. Buffer solutions are therefore used as a means of keeping pH at a nearly constant value in a wide variety of chemical applications, including e.g. chromatography, filtration, etc. They are in particular used to prepare solutions of proteins, which are highly sensitive to changes in pH. In general, a buffer solution may be made up of more than one weak acid and its conjugate base. For instance, a wider buffer region may be created by mixing two buffering agents with overlapping individual buffer regions.

A buffer solution having a desired pH, and optionally also ionic strength, may be prepared by calculating the necessary amounts of the ingredients of the buffer and mixing them. While it is often necessary to solve several different equations for calculating the pH of a relatively simple mixture of a weak acid (or base) and a strong base (or acid) depending on their relative concentrations, there is commercial software available for performing such calculations. For many applications, it would be desirable to also be able to predict the expected solubility of the buffer to be prepared. However, due to the complex nature of buffers solutions, being combinations of strong electrolytes like salts and strong acids or bases that dissociate completely and weak electrolytes like buffer substances that ionize partially, this has so far generally not been possible.

Accordingly there is a need for methods allowing accurate predictions of buffer solubilities. There is also a need for systems to prepare highly concentrated buffer stock solutions without risk for precipitation.

SUMMARY OF THE INVENTION

One aspect of the invention is to provide a method of reliably predicting solubility limits for buffers. This is achieved with a method as defined in the claims.

One advantage is that the method allows predictions also in the presence of high salt concentrations which are commonly used in buffers for e.g. bioprocess separations. Further advantages are that the activities of the ions are taken into account and that the method is easily performed in a computer.

A second aspect of the invention is to provide a computer program for prediction of buffer solubility limits. This is achieved with a program as defined in the claims.

A third aspect of the invention is to provide a mixing system for preparation of buffers. This is achieved with a system as defined in the claims.

A fourth aspect of the invention is to provide a use of solubility predictions for controlling a buffer formulation or in-line dilution system. This is achieved with a use as defined in the claims.

Further suitable embodiments of the invention are described in the dependent claims.

DETAILED DESCRIPTION OF THE INVENTION

Unless defined otherwise, all technical and scientific terms used herein have the same meaning as commonly understood by a person skilled in the art related to this invention. Also, the singular forms "a", "an", and "the" are meant to include plural reference unless it is stated otherwise.

In order to facilitate an understanding of the disclosed invention, a number of terms will be defined below.

Definitions

Buffer

As used herein, a buffer solution is an aqueous solution comprising a mixture of a weak acid and its conjugate base or a weak base and its conjugate acid. It has the property that the pH of the solution changes very little when a small amount of strong acid or base is added to it. Buffer solutions are used as a means of keeping pH at a nearly constant value in a wide variety of chemical applications Titrand and Titrant As used herein in the context of buffer systems, a titrand is the solution (or other substance) into which a titrant is added. The titrand may, for example, be a weak acid or base, and the titrant a strong base or acid, respectively.

Electrolyte

A "strong" electrolyte is a solute hat completely, or almost completely, ionizes or dissociates in a solution. These ions are good conductors of electric current in the solution. Examples of strong electrolytes include, for instance, salts, such as sodium chloride; strong acids, such as hydrochloric acid, sulfuric acid, nitric acid; and strong bases, such as potassium hydroxide, sodium hydroxide, calcium hydroxide.

A weak electrolyte, on the other hand, dissociates into ions only to a small extent, typically much less than 10%, and the vast bulk of the weak electrolyte remains in its original unionized form in solution. In general, most organic acids and their salts, and the salts of organic bases, are weak electrolytes. Examples of weak electrolytes include, for example acetic acid and citric acid and salts thereof. The amount of weak electrolyte that dissociates depends on the number of counter-ions present in the solution.

Conductivity (Electrolytic)

The conductivity (or specific conductance) of an electrolyte solution is a measure of its ability to conduct electricity. The SI unit of conductivity is "siemens" per meter (S/m). Conductivity can be measured by conductometers well known in the art, typically at a temperature of 20° C. or at the temperature where the solution is to be used.

Ionic Strength

The ionic strength of a solution is a function of the concentration of all ions in the solution (half the sum of concentration multiplied by the square of ionic charge for all ions). The ionic strength is typically given in the unit mol/dm$^3$.

Solubility

The solubility of a species is the concentration of the species in a solution at equilibrium with the solid species. Normally this is the maximum concentration attainable in the solution before precipitation of the solid species occurs. The solubility of a buffer is the maximum total concentration of the solutes in the buffer attainable before precipitation of any solid species occurs.

Description of the Method of the Invention

In one aspect the present invention relates to the prediction of the solubility of a buffer solution prepared according to a desired recipe or formula or to a predetermined pH. The invention further relates to a method of preparation of a buffer, including the solubility prediction.

Figure 3:
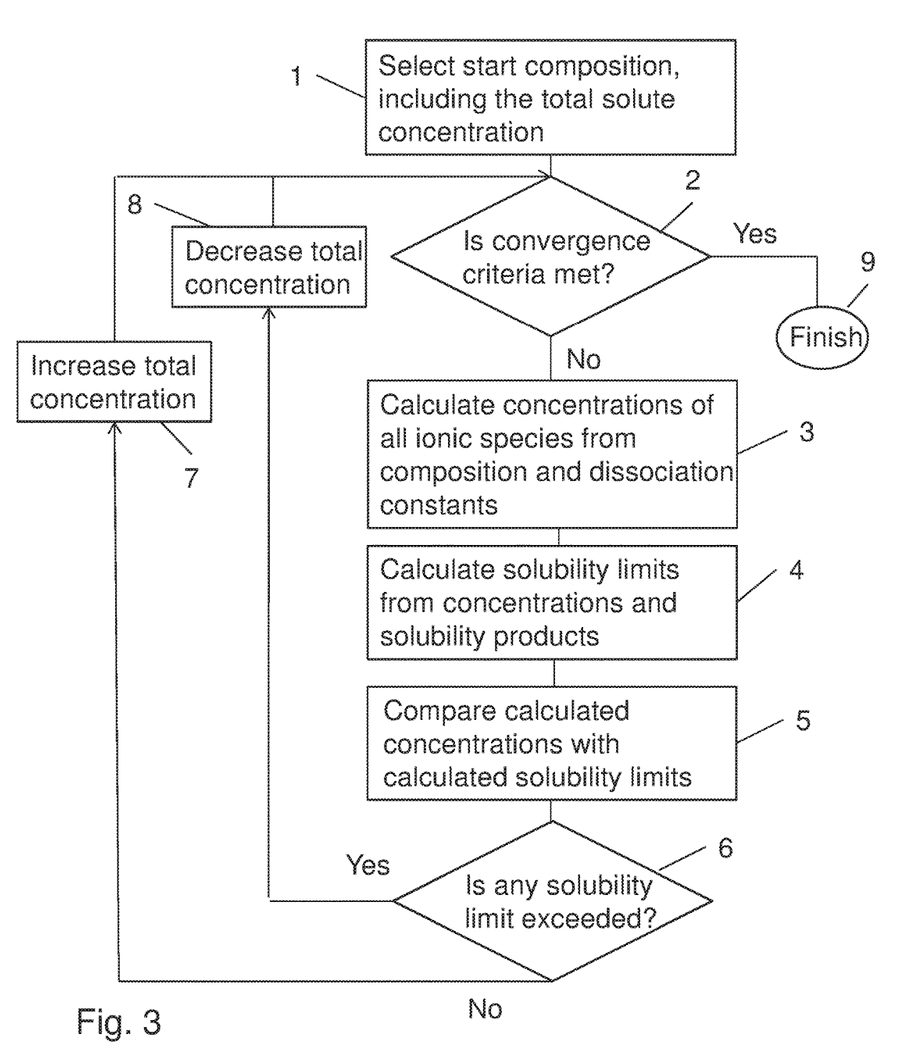
FIG. 3 is a flow diagram of the method of the invention.

The method predicts the solubility of at least one species at a specified pH value (and optionally temperature) in an aqueous buffer, which comprises at least one weak acid species and/or at least one weak base species, and the method comprises, as illustrated in FIG. 3, the steps of:
a) selecting 1 a start composition of the buffer, giving a start value for the total solute concentration, to be used in an iterative procedure;
b) calculating 3 the concentrations of all ionic species present in the buffer at the specified pH value (and optionally temperature) from the total composition of the buffer and available dissociation constants. The concentrations can be calculated by solving the dissociation equilibria equations, using the amounts determined from the buffer total composition as input data;
c) calculating 4 the solubility limits of each combination of ionic species present in the buffer from available solubility products, taking the concentrations calculated in step b) into account;
d) comparing 5 the concentrations of all ionic species calculated in step b) with the solubility limits calculated in step c) and determining 6 if any solubility limit is exceeded;
e) if no solubility limit is exceeded, increasing 7 the total solute concentration of the buffer or, if at least one solubility limit is exceeded, decreasing 8 the total solute concentration of the buffer, and;
f) repeating steps b)-e) until a predetermined convergence criteria is met 2,9.

In some embodiments, the concentrations of the ionic species in step b) are calculated using the equation of Debye-Hückel as further explained below, wherein the ionic strength of all species is used as a weighting parameter in the calculation of an average hydrated radius of the ionic species. In step e), the amount of concentration increase/decrease may be a predetermined constant amount, but it may also be a dynamic function, e.g. starting with a predetermined amount and diminishing the increase/decrease amounts according to a predetermined pattern as the convergence criteria is approached.

In certain embodiments, the method further comprises a step g) of preparing said buffer at the total solute concentration obtained when the convergence criteria is met. Alternatively, the buffer can be prepared to a specified percentage of this concentration, e.g. 60-99%, 80-99% or 90-99% of the total solute concentration obtained when the convergence criteria is met. This ensures a suitable safety factor towards precipitation.

In some embodiments, the method also comprises a step h) of using the buffer prepared in step g) as a stock solution for preparation of a working buffer by dilution of said stock solution.

To prepare a buffer having a desired pH, the added amounts of moles of titrand, titrant, and salt solution, when required, can be calculated. From these mole values, the volume needed from corresponding stock solutions can in turn be calculated. Typically, such calculations are performed by suitable computer software, which is commercially available. The use of such software permits the preparation of buffers up to concentrations of 1 M or higher, as will be described in more detail below.

However, to predict the expected solubility of the buffer to be prepared is not trivial. While for simple electrolytes like NaCl theoretical accounts have been developed, this is generally not applicable to buffers which typically are complex combinations of, on the one hand, strong electrolytes like strong acids or bases and salts which dissociate completely, and weak electrolytes like buffer substances (weak acids and bases) that ionize partially. Before describing the present invention in more detail, the theory behind solubility will be briefly described (http://chemed.chem.purdue.edu/genchem/topicreview/bp/ch18/ksp.php or D A Skoog, D M West: Fundamentals of analytical chemistry 3$^{rd}$ Ed., N.Y. 1976, p. 27-30).

The solubility product equilibrium constant $K_{sp}$ for a salt is the product of the concentrations of the ions, with each concentration raised to a power equal to the coefficient of that ion in the balanced equation for the solubility equilibrium. $K_{sp}$ values for different salts are readily available e.g. in L G Sillén, A E Martell: Stability constants of metal-ion complexes, Chemical Society 1971. If a $K_{sp}$ value is not available for a certain temperature, it can either be interpolated from tabulated data or predicted from data at other temperatures using known enthalpy values according to methods well known in the art.

For instance for silver chloride the solubility equilibrium is given by and the value of Ksp is the equilibrium constant of this equation and is given by $$K_{sp}=[Ag^+][Cl^-]$$

When the formula for a salt contains more than just one of each ion, the solubility product equation is more complex (http://dl.clackamas.cc.or.us/ch105-05solubili.htm). When $PbCl_2$ is dissolved in water for example, two ions of $Cl^-$ are released for every one ion of $Pb^{2+}$.

$$PbCl_2(s) \rightleftarrows Pb^{2+} + 2Cl^-$$

And the solubility product is then:

$$K_{sp} = [Pb^{2+}][Cl^-]^2$$

In the expression above for Ksp the concentration of $Cl^-$ is raised to the power of 2 because the balanced equation for the reaction has the number 2 as coefficient of $Cl^-$. Going from the general case examples to a phosphate buffer, two salts that are commonly used to do these buffers are $NaH_2PO_4$ and $Na_2HPO_4$. The solubility values for these salts are (http://www.merck-chemicals.com/http://www.sigmaaldrich.com/technical-service-home/product-catalog.html) 4.99 and 0.54 M respectively. From its definition, the values of $K_{sp}$ is are calculated in Table 1.

TABLE 1

Calculated values of $K_{sp}$ for $NaH_2PO_4$ and $Na_2HPO_4$

| Buffer salt | Solubility x (M) | $K_{sp}$ |
|---|---|---|
| $NaH_2PO_4$ | 4.99 | x * x = 24.90 |
| $Na_2HPO_4$ | 0.54 | $(2x)^2$ * x = +0.630 |

The solubility for a chemical is decreased if the chemical is dissolved with other compounds that have an ion in common; this is because of the common ion effect (http://en.wikipedia.org/wiki/Common-ion_effect). $Na_2HPO_4$ and $NaH_2PO_4$ are two compounds with $Na^+$ as a common ion. This leads to lower solubility for each of the including chemicals. Furthermore, this effect will lead to a lower maximum buffer concentration. If the solution also includes NaCl, the effects on solubility will be even greater. Using the data from Table above, it can be numerically calculated how much the decrease of solubility of $Na_2HPO_4$ and $NaH_2PO_4$ will be by introducing c molar additional common ions other that the counter-ions of the buffer salt in question. This is done by replacing the left hand side of the equations for $K_{sp}$ with a new quadratic or cubic function of the new solubility. If the new value of solubility in the presence of common ions from other salts is y, this value can be obtained by solving the equations (Table 2)

TABLE 2

| Buffer salt | Solubility y (M) with additional c (M) Na ions | $K_{sp}$ |
|---|---|---|
| $NaH_2PO_4$ | <4.99 | (y + c) * y = 24.90 |
| $Na_2HPO_4$ | <0.54 | $(2(y + c))^2$ * y = +0.630 |

According to the present invention there is now suggested a novel approach for predicting solubility of a buffer as function of its pH value, which is based, on the one hand, on the assumption that even if the buffering substance itself is not a strong electrolyte, every and each one of its charged subspecies can be considered as one strong electrolyte at equilibrium, and, on the other hand, on using the equilibrium concentrations to compare it to the molar solubility values of the buffer or weak electrolyte subspecies as calculated above for the phosphate subspecies, wherein the total amount of counter ions as wells as the concentration of each subspecies has been obtained by solving the equilibrium equation, typically by using an algorithm taking into consideration the activity of the solution as described in more detail below.

Solving Equilibrium Equations

The first step of determining the concentrations of the different ions present in the solution includes solving the equilibrium equations for the buffering species as discussed in the following.

For a particular basic species (which may be a base B or a conjugate base $A^-$) in equilibrium with a corresponding acidic species (which may be a conjugate acid $BH^+$ or an acid HA, respectively) the following equation applies $$pH = pK_a + \log\{(\text{basic species})/(\text{acidic species})\} \quad (Eq. 4)$$

which is often referred to as the Henderson-Hasselbach equation, where $pK_a$ values for particular $B/BH^+$ or $A^-/HA$ pairs can be found in the literature, e.g. in Calbiochem™ Buffers—A guide for the preparation and use of buffers in biological systems, EMD Biosciences 2006 or in D A Skoog, D M West: Fundamentals of Analytical Chemistry $3^{rd}$ Ed., N.Y. 1976, p. 784-785. Also $pK_a$ values can be calculated for different temperatures using methods well known in the art. In Eq. 4, the parentheses denote the activity of each species rather than the concentration, the reason being that the ions involved tend to become shielded from the environment. The activity of each ion is related to the corresponding concentration through the activity coefficient φ

$$(\text{species}) = \varphi[\text{species}] \quad (Eq. 5)$$

In the ideal state of infinite dilution, φ becomes 1 and the activity of every ion will be equal to the corresponding concentration. However, in practice, the ionic strength is different from zero and the activity coefficients of the different species will be less than 1.

Inserting Eq. 5 into Eq. 4 above gives the pH in terms of the concentrations instead of activities $$pH = pK_a' + \log\{(\text{basic species})/(\text{acidic species})\} \quad (Eq. 6)$$

where $$pK_a' = pK_a + \log \varphi_b - \log \varphi_a \quad (Eq. 7)$$

in which $\varphi_a$ and $\varphi_b$ are the activity coefficients for the acidic and basic species, respectively, and $pK_a'$ is an apparent $pK_a$ value which allows the use of the measurable concentrations of the different buffer species.

A model for these deviations is given in the so-called Debye-Hückel theory, known as $$\log \varphi = (AZ^2 I^{0.5})/(1 + 0.33 * 10^8 a I^{0.5}) \quad (Eq. 8)$$

wherein A is a constant, or rather a temperature dependent parameter ~0.51. Using well known data, the value of A can accurately be calculated as $A = 0.4918 + 0.0007*T + 0.000004*T^2$, where T is the temperature in degrees Celsius, Z is the charge of the ion and the quantity a, the radii of the hydrated ions (in Å), is described as the "mean distance of approach of the ions, positive or negative" in the original paper of Debye and Hückel (P Debye, E Hückel: Physikalische Zeitschrift 24: 185-206, 1923).

The value of $pK_a'$ can be calculated by inserting Eq. 8 into Eq. 7 giving $$pK_a' = pK_a + (AZ_a^2 I^{0.5})/(1 + 0.33*10^8 a_a I^{0.5}) - (AZ_b^2 I^{0.5})/(1 + 0.33*10^8 a_b I^{0.5}) \quad (Eq. 9)$$

where the subscripts a and b specify the parameters corresponding to the acid and the base respectively, $Z_a$=charge of acidic species, $Z_b$=charge of basic species, $a_a$=ion size parameter of the acidic species, and $a_b$=ion size parameter of the basic species.

As to the parameter a, Guggenheim E. A. & Schindler, T. D., (1934) *J. Phys. Chem.* 33. 533 suggests an approximation of the parameter a set to 3 Å for all buffer molecules, leading to the simplified formula $$pK_a' = pK_a + (AZ_a^2 I^{0.5})/(1+I^{0.5}) - (AZ_b^2 I^{0.5})/(1+I^{0.5}) \quad \text{(Eq. 10)}$$

Eq. 10 above is the formula for ionic strength correction usually found in the literature.

Using Eq. 7 (or 4) in combination with the equations for (i) the conservation of mass, (ii) the conservation of charge, and (iii) the water dissociation equilibrium, the concentrations of the acidic and basic species, respectively, of a monoprotic buffer at equilibrium may be calculated.

However, many buffers are polyprotic, i.e. their buffer molecules can accept and give away more than one proton corresponding to more than one $pK_a$ value. The number of species in such a buffer system is always one more than the number of $pK_a$ values. The calculation of the amount of moles in each of the protonation species is equivalent to solving the equilibrium equations of each of the species with the "neighbouring" species with one more and/or one less proton and with the concentration of hydrogen atoms (the pH).

Assume, for example, a tritropic buffer. Four protonation states or species will be defined (s1, s2, s3 and s4), and three $pK_a$ values. Three equations (corresponding to three $pK_a$ values) may then be derived directly from Eq. 6 above.

$$xx[i] = 10^{(pH-pKa[i])} \quad \text{(Eq. 11)}$$

where each i corresponds to each $pK_a(i)$ value (i=1, 2, 3), and xx[i] are the ratios between the concentrations of the corresponding base and the corresponding acid i.e. $xx[1]=[s_2/s_1]$, $xx[2]=[s_3/s_2]$, $xx[3]=[s_4/s_3]$.

In addition to these three equations, an equation arises because of the conservation of mass $$[s_1]+[s_2]+[s_3]+[s_4]=\text{buffer concentration} \quad \text{(Eq. 12)}$$

and the conservation of charge $$[H^+]-[OH^-]+\Sigma \text{ specific charge } (s_i)-\text{titrant\_charge}^* [\text{titrant}]-\text{spec\_charge(start\_species)}^*[\text{start\_species}]=0 \quad \text{(Eq. 13)}$$

By "start_species" is meant the species of the buffer substance before mixing, i.e. the protonation state of the buffer in the can or stock solution. This protonation state is determined by the amount of counter-ions per buffer molecule because the macroscopic object, can or stock solution, has to be electrically neutral. The minus sign in front of [OH⁻] is due to the minus sign of the charge of the OH ions, whereas the minus sign in front of the two last terms is due to the charge of the counter-ions of the titrant and the start species, respectively.

Finally, there is the water dissociation equilibrium $$[OH^-][H^+] = 10^{14} \quad \text{(Eq. 14)}$$

Equations (11) to (14) above imply that there are six equations with six unknowns (the four [$s_i$], [OH⁻] and [H⁺]) for the case of three $pK_a$ values, and the equilibrium concentrations of the respective acidic and basic species may thus be calculated.

For a monoprotic buffer, for example, the calculations are simplified; $s_1$ corresponds to the acidic species, $s_2$ to the basic species and the concentrations of $s_3$ and $s_4$ are set to zero.

A more accurate determination of the ion size parameter a in the Debye-Hückel equation 8 above is described in WO2009/131524A1 (the disclosure of which is incorporated by reference herein), where a is determined as the weighted mean ion size of all species contributing to the ionic strength of the liquid mixture, using the ionic strength as weighting parameter. The ion size parameter a may then be calculated as $$a = \frac{\sum I_i a_i}{I} \quad \text{(Eq. 15)}$$

where $I_i$ is the ionic strength, $a_i$ is the ion size parameter of species i, and I is the total ionic strength defined by $$I = \tfrac{1}{2}\Sigma(C_i Z_i) \quad \text{(Eq. 16)}$$

where $C_i$ is the concentration and is the charge of ion present in the solution (in units of electronic charge), which gives $$I_i = \tfrac{1}{2} Z_i^2 C_i \quad \text{(Eq. 17)}$$

The ion size parameter a may also be approximated as $$a = 0.5*(\text{mass})^{1/3} + \text{shell} \quad \text{(Eq. 18)}$$

where "shell" is fixed at a specific value for a positively charged ionic species (typically in the range of 3.9-4.1), and at another fixed value for a negatively charged species (typically in the range of 0-0.1, or 0).

This permits the determination of the relative proportions of the constituents of buffers having salt concentrations up to or above 2 M or even 5 M.

In the above-mentioned WO 2009/131524 A1 there is also disclosed a computer program, or software, for calculating a recipe (i.e. amounts of titrand, titrant, water and salt) to achieve a solution of a given pH and ionic strength (or, alternatively, salt concentration instead of ionic strength). Specifically, a computer program "Buffalo Plus" is disclosed which is written in Visual C++ and can be run in Windows for accurate calculation of buffer pH at ionic strengths as high as 1 M for buffer systems including phosphate, citrate, acetate and Tris. Such software may conveniently be used for calculating the equilibrium concentrations of acidic and basic species for the purposes of the present invention.

Predicting Solubility

Using this approach, in brief, by first determining the exact concentrations of the different ions present in solution including the concentration of each of the charged species of the buffer substance, the solubility can then be calculated.

According to the present invention, the prediction of the solubility of a buffer comprises an iterative procedure where the concentration of the buffer or weak electrolyte is varied in steps starting from an arbitrary start value. The size of the step is varied during the procedure being larger at the beginning and smaller at the end. For every buffer concentration the procedure implies the following steps. i) Solving the exact concentrations of the different ions present in the solution including the equilibrium concentration of each of the subspecies of the buffer or weak electrolyte for the specified pH value. ii) Determining the molar solubility of each of the charged species of the buffer or weak electrolyte by taking into consideration the common ion effect which means taking into considerations all the counter ions present in the solution. iii) Comparing the molar concentration of each of the charged species of buffer or weak electrolyte to the molar solubility and deciding upon this comparison whether to increase or decrease the concentration in the next step. If the solubility of each and every of the present subspecies is larger than the concentration of the corresponding subspecies then the buffer concentration is increased. Otherwise it is decreased. The procedure stops when the step is lower than a value specified beforehand.

This value is an estimate of the accuracy of the solubility of the buffer according to the method.

An alternative procedure is to do the calculations for all buffer concentrations differing by a pre-defined distance in a buffer concentration interval. The solubility of the buffer is then obtained as a value close to the concentration where the solubility of at least one subspecies is lower than the corresponding concentration of the buffer subspecies.

The method of the invention may be implemented by software run on an electrical data processing device, such as a computer. Such software may be provided to the computer on any suitable computer-readable medium, including a record medium, a read-only memory, or an electrical or optical signal which may be conveyed via electrical or optical cable or by radio or other means.

Predicting solubility of a buffer at a given pH as described above may be used for several purposes. Exemplary applications include the use for controlling a buffer formulation system or an in-line dilution system by determining the maximum concentration for a formulated buffer. Another example is an in-line dilution system where it is of great value to know the highest concentration of the buffer to be diluted. This concentration can be equal to the solubility value or for convenience a fraction of this value for example 80%, 60% or other fraction of the solubility. In-line dilution systems usually operate by mixing a previously prepared buffer concentrate with water (typically water for injection) immediately before a second operation such as a chromatography step, buffer exchange step etc. The concentrate should have as high concentration as possible without causing precipitation, but so far this has necessitated extensive testing of many different compositions to find suitable concentrations with acceptable safety margins. Alternatively, excessive safety margins have been used, necessitating the use of overly large concentrate tanks and the preparation of excessive volumes of concentrate. With the new method of solubility prediction, highly concentrated buffers can be prepared with acceptable safety margins. It also allows for predictions to be carried out for several temperatures, allowing the determination of suitable safety margins taking account of the entire temperature range expected during preparation, storage and use of the concentrate.

Predictions of solubility according to the methods of the invention may also be used in screening experiments wherein concentration is used as a design of experiment (DoE) parameter where it is of great value to know the highest concentration that is possible to achieve.

Figure 4:
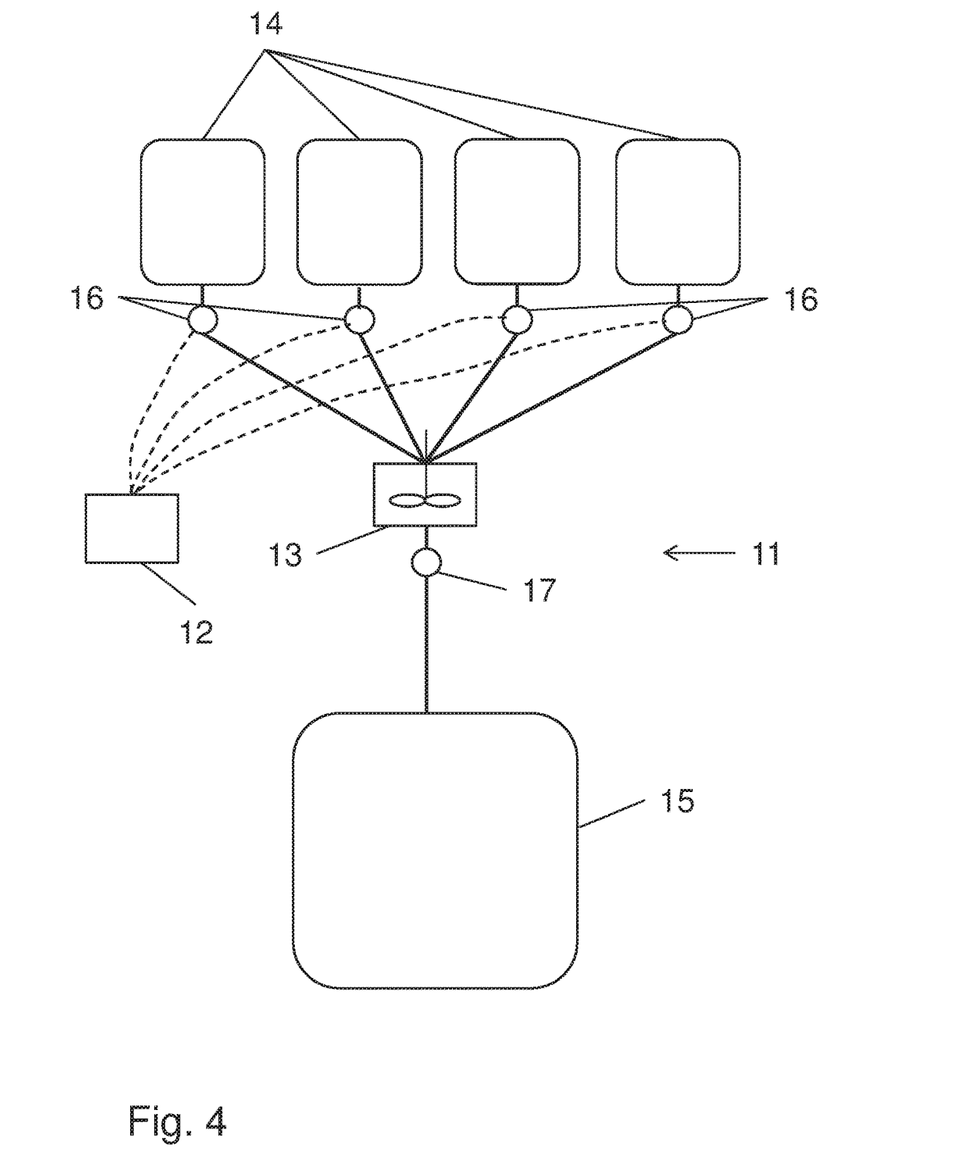
FIG. 4 shows a mixing system of the invention.
Figure 5:
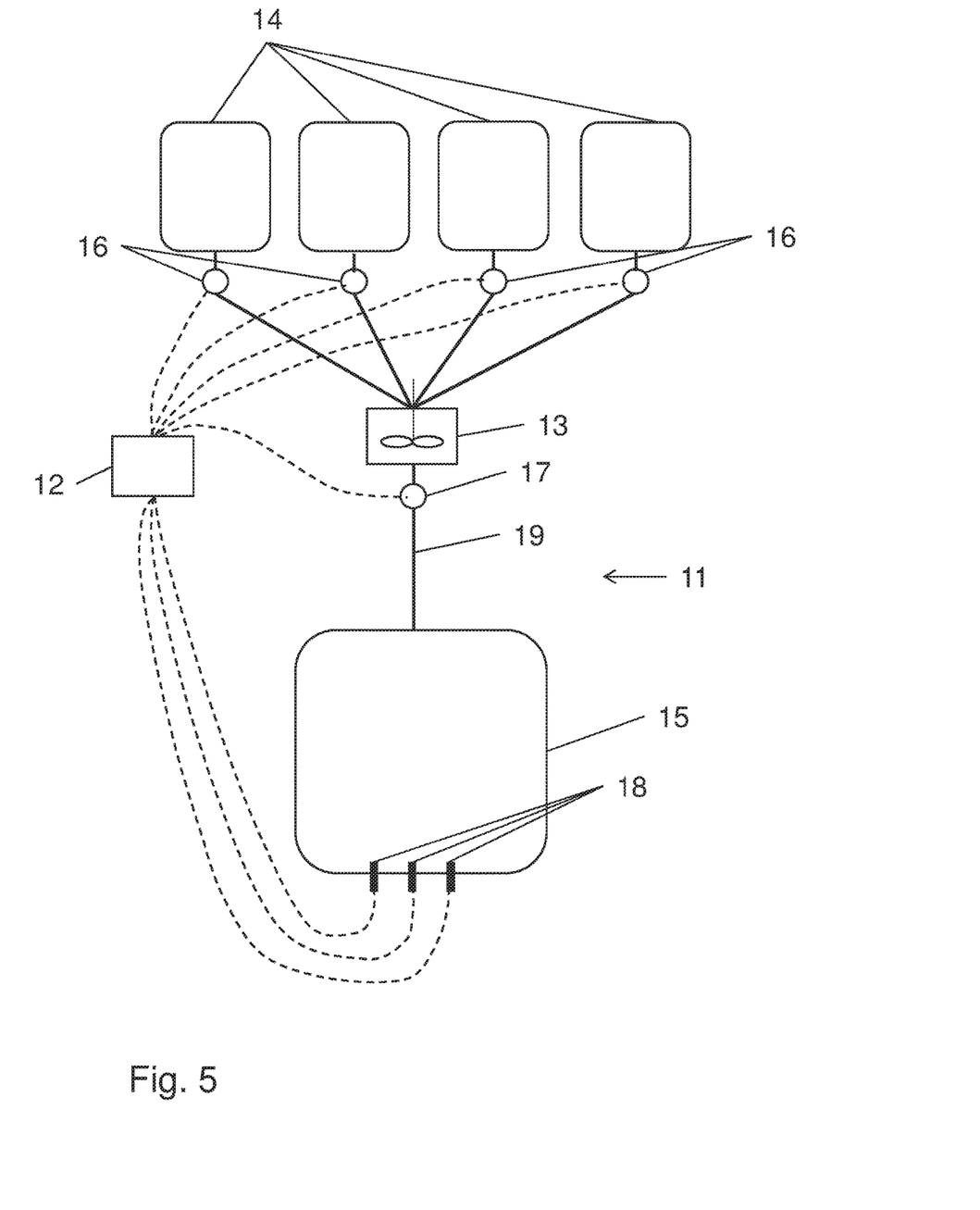
FIG. 5 shows a buffer formulation mixing system for use with the invention.
Figure 6:
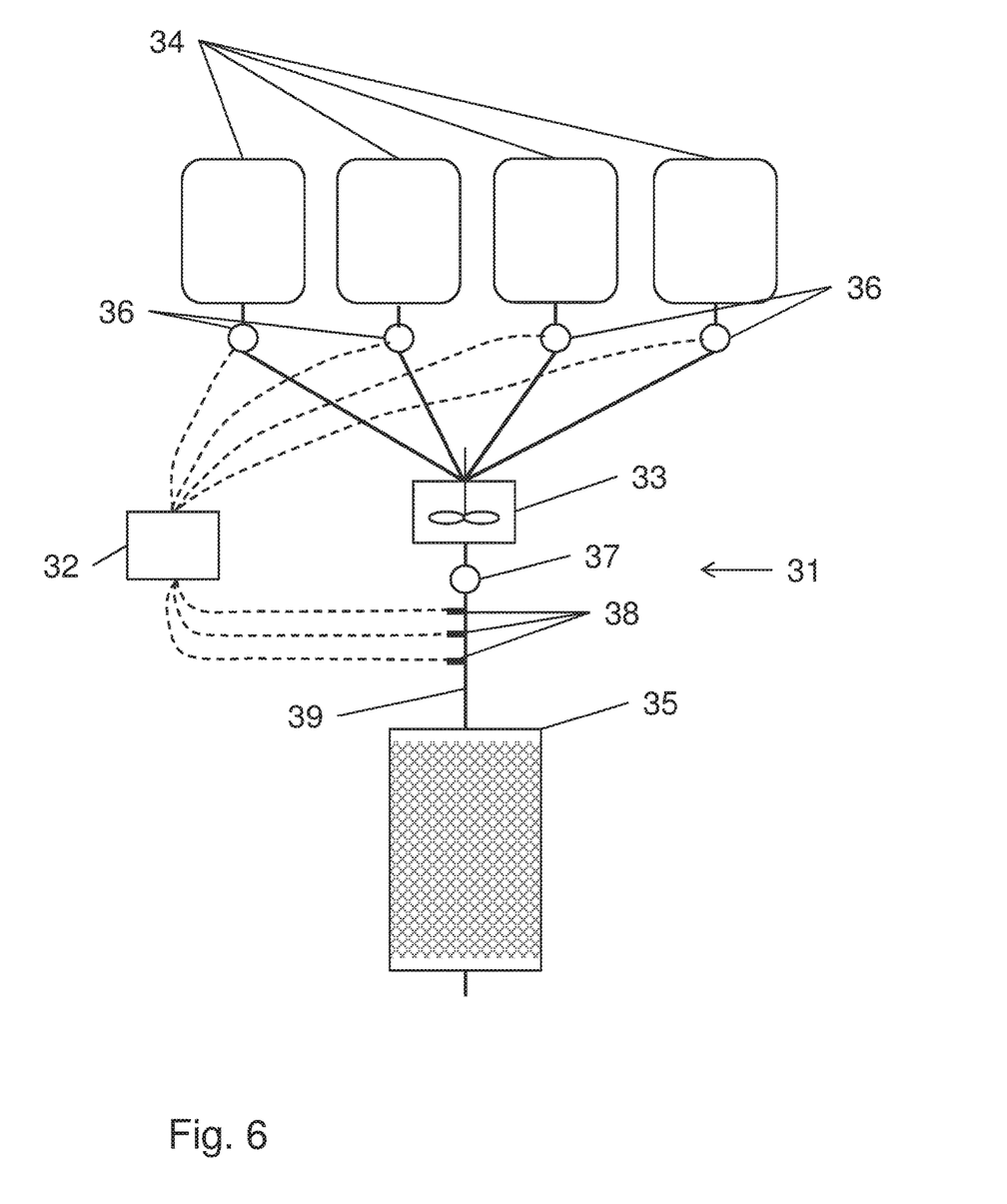
FIG. 6 shows an in-line conditioning mixing system for use with the invention.

In one aspect, illustrated by FIGS. 4-6, the present invention discloses a mixing system 11;31 configured to carry out the methods described above. The mixing system comprises a control unit 12;32, a mixer 13;33 and at least two component tanks 14;34, fluidically connected to the mixer. The control unit can suitably be a computer, programmed to perform the solubility prediction as described above. The component tanks can contain stock solutions of buffer components, which are then mixed by the mixer in proportions controlled by the control unit and either conveyed into a storage tank 15 (for a buffer formulation system) or directly into e.g. a chromatography column 35, a chromatography system or other equipment for use in a separation process (e.g. for an in-line conditioning system), which are fluidically connected to the mixer. The stock solutions can e.g. be conveyed to the mixer by component pumps 16;36, which can suitably be metering pumps, such as piston pumps, diaphragm pumps or peristaltic pumps. The component pumps are suitably electrically or electromagnetically coupled to the control unit and controlled by the control unit to provide a buffer composition calculated by the methods described above, e.g. such that the concentration is a fraction of the solubility limit such as 60-99% or 80-99% of the solubility limit or of the total solute concentration obtained when the convergence criteria is met. The mixer can be a passive mixer (i.e. a mixer without moving parts), such as a static mixer, or it can be a mixer with moving parts, e.g. an impeller-driven mixer. From the mixer, the mixed buffer is conveyed to the storage tank or to further equipment such as a chromatography system, either by a buffer pump 17;37 or by gravity flow. The buffer pump may also be electrically or electromagnetically coupled to the control unit and controlled by the control unit.

The mixing system may also be equipped with one or more sensors 18;38, e.g. pH, conductivity, temperature and/or precipitation sensors. Such sensors may e.g. be located in the storage tank 15 or in a conduit 19;39 downstream from the mixer and can be used to monitor and document the actual composition and/or properties of the buffer. They can suitably be electrically or electromagnetically connected to the control unit and their signals may optionally be used in additional feedback loop control of the component pumps 16;36, e.g. for fine adjustment of the buffer composition. pH, conductivity and temperature sensors are well known in the art and the precipitation sensor can e.g. be an optical turbidity sensor or other type of sensor suitable for detecting particles in a liquid.

The invention will now be described in more detail, by way of example only, by the following non-limiting Example.

Example

In this example, the solubility of a phosphate buffer was calculated for all the pH values in the range between 4.7 to 8.0 using the new method. This was done both in the presence and in the absence of 1M NaCl in the solution. First the molar solubility of $Na_2HPO_4$ and of $NaH_2PO_4$ was calculated as function of the concentration of the additional concentration of Na+ ions (i.e. solving for y in Table 2 above). This was done for a number of discrete points according to Table 3 and Table 4 below. For the actual solution of the quadratic and cubic equations an on-line equation solver (http://www.akiti.ca/Quad3Deg.html) well known in the art was used.

TABLE 3

Calculated $Na_2HPO_4$ solubility

| Conc. Na+ ions | Solubility $Na_2HPO_4$ |
|---|---|
| 0.01 | 0.538677 |
| 0.02 | 0.535359 |
| 0.04 | 0.528755 |
| 0.1 | 0.509195 |
| 0.15 | 0.493194 |
| 0.2 | 0.477473 |
| 0.3 | 0.446899 |
| 0.5 | 0.389428 |
| 1 | 0.269148 |
| 1.5 | 0.1829385 |
| 2 | 0.125659937 |
| 2.5 | 0.0888301 |
| 3 | 0.065009566 |

TABLE 4

Calculated Na$_2$HPO$_4$ solubility

| Conc. Na$^+$ ions | Solubility NaH$_2$PO$_4$ |
|---|---|
| 0.01 | 4.893982 |
| 0.02 | 4.88899 |
| 0.04 | 4.87902 |
| 0.1 | 4.849235 |
| 0.15 | 4.824554 |
| 0.2 | 4.8 |
| 0.3 | 4.751275 |
| 0.5 | 4.655354 |
| 1 | 4.424429 |

Figure 1A:
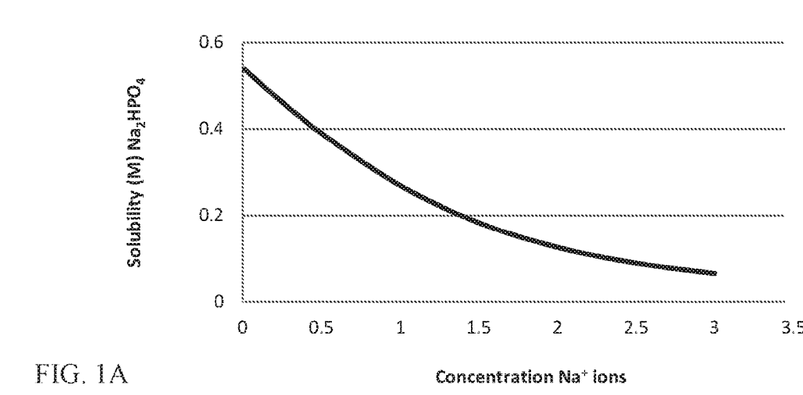
FIG. 1a) is a graph showing the calculated solubility of $Na_2HPO_4$ as a function of the concentration of $Na^+$ ions.
Figure 1B:
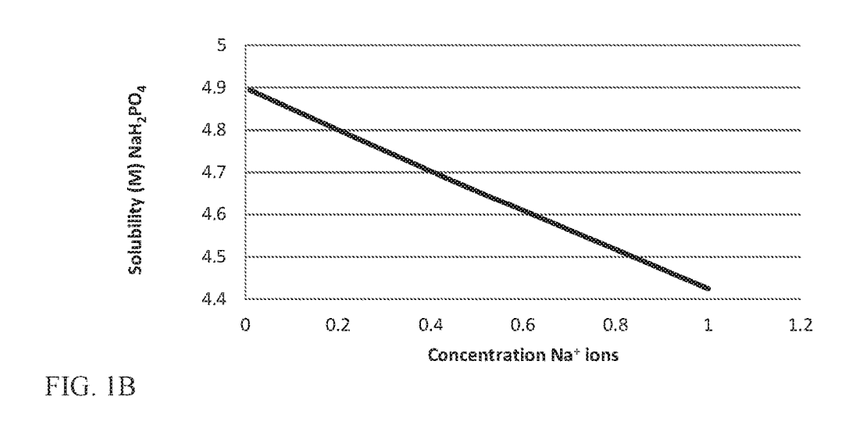
FIG. 1b) is a graph showing the calculated solubility of $NaH_2PO_4$ as a function of the concentration of $Na^+$ ions.

The data was plotted and simple quadratic equations were fitted to the plots (FIGS. 1a) and b))

Then the solubility of phosphate was calculated according to the method for a discrete number of pH values (Table 5) For the actual determination of each ionic and buffer species at every single pH and buffer concentration a program using an algorithm previously described (WO2009131524A1) was used.

TABLE 5

Calculated solubilities for phosphate buffers with and without 1M NaCl.

| Phosphate (pH 5.8-8) | Phosphate | Phosphate with 1M NaCl |
|---|---|---|
| 4.82 | 1917 | 1269 |
| 5.3 | 1508 | 906 |
| 5.8 | 1137 | 622 |
| 6 | 1024 | 532 |
| 6.2 | 925 | 456 |
| 6.4 | 836 | 406 |
| 6.6 | 759 | 366 |
| 6.8 | 695 | 336 |
| 7 | 647 | 315 |
| 7.2 | 612 | 301 |
| 7.4 | 588 | 291 |
| 7.6 | 571 | 285 |
| 7.8 | 561 | 281 |
| 8 | 554 | 279 |

Figure 2:
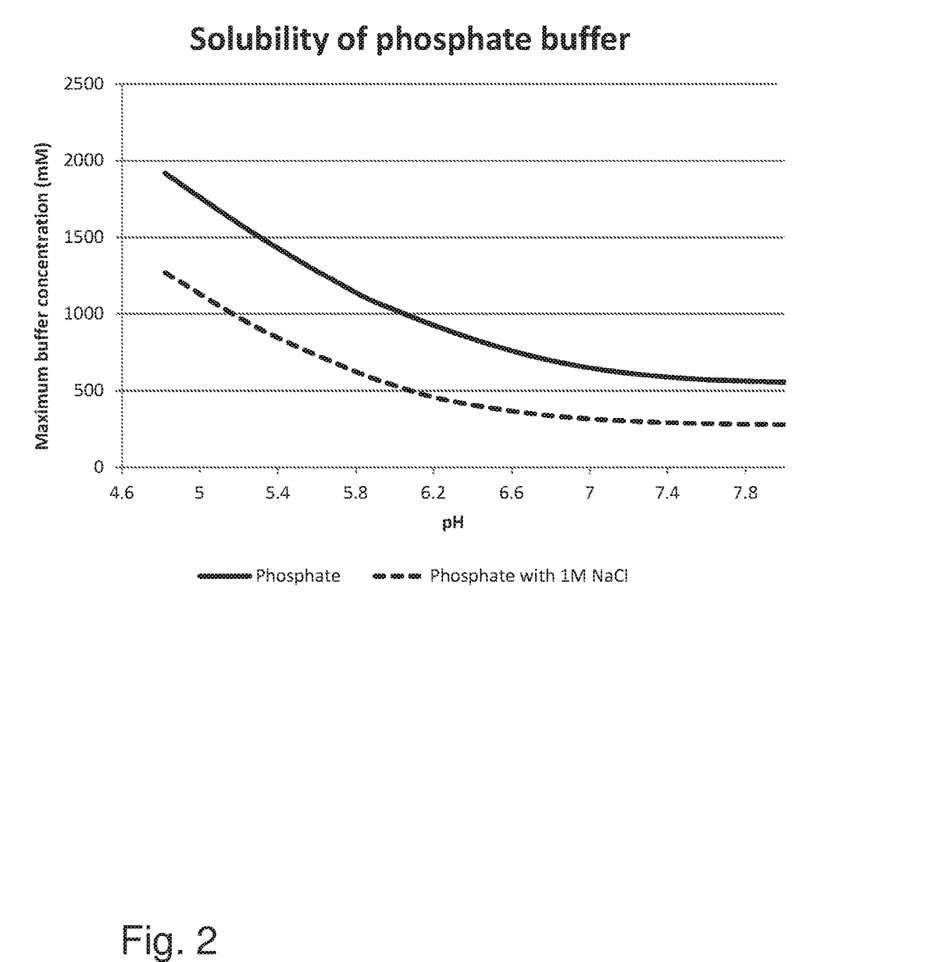
FIG. 2 is a graph showing the solubility of a phosphate buffer with no NaCl added and also of a phosphate buffer containing 1M NaCl.

The results are plotted in FIG. 2.

The total solubility for each pH was calculated according to the method comprising an iterative procedure where the concentration of the buffer was varied in steps starting from a low value. The size of the step was varied during the procedure being larger at the beginning and smaller at the end. For every buffer concentration the procedure implied the following steps. i) Solving the exact concentrations of the different ions present in the solution including the equilibrium concentration of each of the subspecies of the buffer or weak electrolyte for the specified pH value using the named program. ii) Determining the molar solubility of each of the charged species of the buffer or weak electrolyte by taking into consideration the addition of ions according to the previous produced Figure iii) Comparing the molar concentration of each of the charged species of buffer or weak electrolyte to the molar solubility and deciding upon this comparison whether to increase or decrease the concentration in the next step. If the solubility of each and every of the present subspecies was larger than the concentration of the corresponding subspecies than the buffer concentration was increased. Otherwise it was decreased. The procedure stopped when the step was lower than a value specified beforehand which in this case was 1 mM.

The method was challenged experimentally by adding equal parts of 4.5M NaH$_2$PO$_4$ and 0.5M Na$_2$HPO$_4$ to make a 2.5M Phosphate buffer pH~5. The experiment was made in triplicate and analyzed visually for precipitation indications, like the formation of crystals.

The experiment gave a total volume of 6 ml in each of the triplicates and precipitate could be seen within a few seconds. This is in agreement with method because the concentration 2.5 M is larger than the solubility (less than 2M as shown in figure at pH~5) for this pH as predicted by the method.

While the above described fitting procedure was done manually, it may conveniently be performed by an algorithm designed therefor. Based on the teaching above, the design of such a suitable algorithm may readily be made by a person skilled in the art.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties as if individually incorporated.

The invention claimed is:

1. A method for predicting the solubility of at least one species at a specified pH value in an aqueous buffer comprising at least one weak acid species and/or at least one weak base species, said method comprising the steps of:
    a) selecting a start composition of the buffer, giving a start value for the total solute concentration;
    b) calculating the concentrations of all ionic species present in the buffer at the specified pH value from the total composition of the buffer and available dissociation constants;
    c) calculating the solubility limits of each combination of ionic species present in the buffer from available solubility products, taking the concentrations calculated in step b) into account;
    d) comparing the concentrations of all ionic species calculated in step b) with the solubility limits calculated in step c) to determine if any solubility limit is exceeded;
    e) in response to determining no solubility limit is exceeded, increasing the total solute concentration of the buffer or, in response to determining at least one solubility limit is exceeded, decreasing the total solute concentration of the buffer;
    f) repeating steps b) e) until a predetermined convergence criteria is met; and
    g) preparing said buffer at the total solute concentration obtained when the convergence criteria is met.

2. The method of claim 1, wherein in step b), the concentrations of the ionic species are calculated using the equation of Debye-Hückel, wherein the ionic strength of all species is used as a weighting parameter in the calculation of an average hydrated radius of the ionic species.

3. The method of claim 2, which is computer-implemented.

4. The method of claim 1, further comprising a step h) of using the buffer prepared in step g) as a stock solution for preparation of a working buffer by dilution of said stock solution, or a step h) of diluting the buffer prepared in step g) to prepare a working buffer.

5. A method for preparation of a buffer by predicting the solubility according to the method of claim 4.

6. A computer program on a readable medium, comprising instructions for causing a computer to perform the method of claim 5 wherein the readable medium is not a signal.

7. A mixing system comprising a control unit, a mixer and at least two component tanks fluidically connected to said mixer, said system being configured to carry out the method of claim 5.

8. The mixing system of claim 7, further comprising at least two component pumps, adapted to convey buffer components from said component tanks to said mixer, wherein said component pumps are electrically or electromagnetically connected to said control unit.

9. The mixing system of claim 8, wherein said mixer is fluidically connected to a chromatography column or a chromatography system.

10. The mixing system of claim 9, further comprising at least one sensor adapted to monitor the composition and/or properties of a mixed buffer downstream of said mixer.

11. The method according to claim 1, further comprising controlling one or more of a buffer formulation system, an in-line conditioning system and an in-line dilution system based on the concentrations of all the ionic species.

12. The method according to claim 11, further comprising preparing a buffer having a total solute concentration corresponding to 60-99% of the predicted solubility, such as 80-99% or 90-99% of the predicted solubility.

13. The method according to claim 11, further comprising preparing a buffer having a total solute concentration corresponding to 60-99% of the solubility limit, such as 80-99% or 90-99% of the solubility limit.

14. The method according to claim 11, further comprising performing a screening experiment based on at least one screening parameter, wherein the at least one screening parameter comprises the total solute concentration.

\* \* \* \* \*